United States Patent [19]

Rovero et al.

[11] Patent Number: 5,128,447
[45] Date of Patent: Jul. 7, 1992

[54] SYNTHETIC PEPTIDE ANTAGONISTS OF NEUROKININ A, SALTS THEREOF AND RESPECTIVE PREPARATION PROCESSES

[75] Inventors: Paolo Rovero; Vittorio Pestellini; Carlo A. Maggi; Riccardo Patacchini, all of Florence; Paolo Santicioli, Arezzo; Sandro Giuliani; Alberto Meli, both of Florence, all of Italy

[73] Assignee: A. Menarini Industrie Farmaceutiche Riunite s.r.l., Florence, Italy

[21] Appl. No.: 528,706

[22] Filed: May 24, 1990

[30] Foreign Application Priority Data

May 29, 1989 [IT] Italy .................. 9432 A/89

[51] Int. Cl.$^5$ .................................. A61K 37/02
[52] U.S. Cl. ........................ 530/328; 530/329; 930/21
[58] Field of Search .............. 530/329, 327, 328; 514/16; 930/21

[56] References Cited

U.S. PATENT DOCUMENTS 4,742,156  5/1988  Wright .
4,801,613  1/1989  Stewart et al. ................ 514/14

OTHER PUBLICATIONS

Regolf et al., *Life Sci* 40, 109 (1987), Specific at P1,132.
Mizrahi et al., CA 104(9) 62801 (1985).

*Primary Examiner*—Lester L. Lee
*Assistant Examiner*—B. Celsa
*Attorney, Agent, or Firm*—McGlew & Tuttle

[57] ABSTRACT

A synthetic peptide corresponding to the following formula:

$$X-Asp-Y-DTrp-Val-DTrp-Z-K-NH_2$$

where:
X = H, Arg, DArg, Lys, DLys, Thr, DThr
Y = Tyr, Trp, DTrp, Ser, Met
Z = Trp, DTrp
K = Arg, Phe, DTrp, Tyr, Met and pharmaceutically acceptable salts thereof with organic and inorganic acids as competitive antagonists against neurokinin A (NK-2 receptor).

8 Claims, No Drawings

SYNTHETIC PEPTIDE ANTAGONISTS OF NEUROKININ A, SALTS THEREOF AND RESPECTIVE PREPARATION PROCESSES

DESCRIPTION

1. FIELD OF THE INVENTION

Neurokinin A, also known as substance K or α-neurokinin, belongs like substance P and neurokinin B to the class of the tachykinins (nomenclature suggested by the IUPHAR Committee, C. Jordan and P. Oehme, Substance P: metabolism and biological actions, Taylor and Francis, London, 1985), consisting of peptides which have the C-terminal sequence Phe-X-Gly-Leu-Met-$NH_2$.

For the nomenclature and the abbreviations of the amino acids, reference is made to the recommendations of the IUPAC-IUB Joint Commission on Biochemical Nomenclature (Eur. J. Biochem. 138, 9, 1984).

Neurokinin A was isolated in 1983 from the spinal cord of pigs (S. Kimura et al., Proc. Jap. Acad. Ser. B, 59, 101, 1983, and K. Kanagawa et al., Biochem. Biophys. Res. Com. 114, 533, 1983) and was characterized as a C-terminal decapeptide amide of the sequence:

H-$Hys^1$-$Lys^2$-$Thr^3$-$Asp^4$-$Ser^5$-$Phe^6$-$Val^7$-$Gly^8$-$Leu^9$-$Met^{10}$-$NH_2$.

This sequence differs from that of substance P by the amino acid in position 7 and by the N-terminal sequence (positions 1–5) and differs from that of neurokinin B by the amino acids in positions 1–3 and 5, always in the N-terminal zone. The structures of substance P and neurokinin B are, respectively:

Substance P:

H-Arg-Pro-Lys-Pro-Gln-Gln-Phe-Phe-Gly-Leu-Met-$NH_2$

Neurokinin B:

H-Asp-Met-His-Asp-Phe-Phe-Val-Gly-Leu-Met-$NH_2$

Peptide antagonists of substance P and of neurokinin B are already known and have been described in U.S. Pat. Nos. 4,481,139 and 4,665,157 respectively; however, no antagonists of neurokinin A are known. It is likewise known (D. Regoli et al., Life Sci. 40, 109, 1987) that the C-terminal heptapeptide fragment of neurokinin A maintains the same biological activity as the complete peptide.

SUMMARY OF THE INVENTION

The subject of the present invention is synthetic peptides of the general formula:

X-Asp-Y-DTrp-Val-DTrp-Z-K-$NH_2$ where:
X=H, Arg, DArg, Lys, DLys, Thr, DThr
Y=Tyr, Trp, DTrp, Ser, Met
Z=Trp, DTrp
K=Arg, Phe, DTrp, Tyr, Met and pharmaceutically acceptable salts thereof obtained with organic and inorganic acids. Such peptides are shown to possess a biological activity as competitive antagonists against neurokinin A, but are free of an agonist action.

More particularly, the subject of the invention is a synthetic peptide corresponding to the following formula:

X-Asp-Y-DTrp-Val-DTrp-Z-K-$NH_2$ where:
X=H, Arg, Lys, Thr
Y=Tyr
Z=DTrp
K=Arg, Phe, DTrp, Tyr, Met as well as pharmaceutically acceptable salts thereof with organic acids and pharmaceutically acceptable salts thereof with inorganic acids.

The following in particular are also part of the invention:

an octapeptide having the following structure:

H-Arg-Asp-Tyr-DTrp-Val-DTrp-DTrp-Arg-$NH_2$;

a heptapeptide having the following structure:

H-Asp-Tyr-DTrp-Val-DTrp-DTrp-Arg-$NH_2$;

an octapeptide having the following structure:

H-Arg-Asp-Tyr-DTrp-Val-DTrp-DTrp-Phe-$NH_2$;

a heptapeptide having the following structure:

H-Asp-Tyr-DTrp-Val-DTrp-DTrp-DTrp-$NH_2$;

a heptapeptide having the following structure:

H-Asp-Trp-DTrp-Val-DTrp-DTrp-Arg-$NH_2$.

Synthetic peptides as defined above are competitive antagonists against neurokinin A (NK-2 receptor).

A further subject of the invention is a process for obtaining the peptides defined above, comprising solid-phase synthesis building up the peptide chain from the C-terminal end towards the N-terminal end on an insoluble polymeric support, and subsequent detachment of the peptide from the polymer support by hydrolysis in anhydrous hydrofluoric acid.

The novel peptides which are the subject of the present application are useful for reducing or antagonizing, in animals and in humans, pathological effects due to an excess of neurokinin A, such as bronchoconstrictions or spasms in the intestines or in the urinary bladder.

DETAILED DESCRIPTION OF THE INVENTION

The peptides which are the subject of the present invention can be prepared by utilizing the techniques known in peptide synthesis, such as are described, for example, in M. Bodanszky and A. Bodanszky, The Practice of Peptide Synthesis, Springer-Verlag, Berlin Heidelberg 1984. By way of non-limiting example, the plan of the synthesis in solid phase according to Merrifield (R.B. Merrifield, J. Am. Chem. Soc. 85, 2149, 1963) is reported. When the alpha-amino function of the amino acids was protected by the t-butoxycarbonyl (Boc) group, 4-methylbenzhydrylamine resin (MBHA; amine groups: 0.4–0.6 mmol/g of resin) can be used as solid support for obtaining C-terminal amides; the side chains of trifunctional amino acids were protected by known methods described in the literature. The peptides were assembled by means of a semiautomatic synthesizer, using the method of symmetrical anhydrides; 1-2 g of resin are placed in the reactor and neutralized with 10% triethylamine in chloroform, and two equivalents of the symmetrical anhydride of the amino acid freshly prepared in solution in 1/1 methylene chloride/dimethylformamide are then added to the reactor. After a 60 minute coupling cycle and a cycle of washings of the resin with methylene chloride and isopropanol, the completeness of the coupling is verified by means of the ninhydrin test according to Kaiser et al., Anal. Biochem. 34, 595, 1970. The removal of the protective group from the amine group of the coupled amino acid is accomplished by treatment with 40% trifluoroacetic acid in methylene chloride and then with 5% diisopropylethylamine in methylene chloride (automatic protective group removal and neutralization cycle) in order to obtain the resin ready for the next coupling which is carried out by the same procedure. After the addition of the last amino acid (N-terminal end) and the elimination of the Boc group (protective group removal cycle with trifluoroacetic acid), the resin is removed from the reactor and dried in vacuo overnight. For the detachment of the peptide from the resin in the form of the C-terminal amide and the simultaneous removal of the protective groups from all the side chains of the amino acids, the resin is treated for 1 hour with 95/5/0.5 anhydrous hydrofluoric acid/anisole/dimethyl sulfide at 0° C. in a "Teflon" reactor. After removal of the hydrofluoric acid in an nitrogen stream, the resin is dried in vacuo and washed with ethyl ether, and the crude peptide is extracted with 50% acetic acid. The acetic acid solution obtained is concentrated in vacuo to a small volume and directly loaded on a column of steric exclusion resin for a first purification cycle; the fractions containing the peptide (characterized by HPLC analysis techniques) are combined, evaporated in vacuo and lyophilized. Finally, the peptide is purified by preparative reverse-phase high-pressure chromatographic techniques, in order to obtain a purity greater than 98%.

EXAMPLE 1

Synthesis of the octapeptide having the following sequence:

H-Arg-Asp-Tyr-DTrp-Val-DTrp-DTrp-Arg-NH$_2$ 2.0 g of MBHA resin (Novabiochem, Switzerland) carrying 0.45 milliequivalents/g of amine groups are placed in the reactor of a Labortec SP 640 semiautomatic synthesizer. The resin is neutralized manually, carrying out two washings (5 min+15 min) with 10% triethylamine in chloroform (2×15 ml) and three washings (3×1 min) with methylene chloride (3×15 ml). This is followed by the coupling of arginine by the preformed symmetrical anhydride technique, with protection of the alpha-amine function by the t-butoxycarbonyl (Boc) group and of the guanidine function on the side chain by the p-toluene-guanidine function on the side chain by the p-toluene-sulfonyl group (tosyl; Tos): 1.54 g of Boc-Arg(Tos)-OH (3.6 milliequivalents) are dissolved in 3 ml of methylene chloride and 4.64 ml of an 8% weight/volume solution of dicyclohexylcarbodiimide in methylene chloride (equal to 1.8 milliequivalents) are added, with continuous magnetic stirring for 15 minutes in an ice bath, the mixture is filtered on a Gooch filter to remove the dicyclohexylurea formed, and the solution is added to the reactor, diluting with a further 5 ml of dimethylformamide and then initiating the automatic coupling cycle (see Table 1). At the end of the cycle described in the table, the Kaiser test is carried out on an aliquot of the resin; if the degree of incorporation of the amino acid is higher than 99%, the automatic removal of the protective group from the amino group is allowed to proceed; otherwise, the coupling is repeated. For the subsequent couplings, always according to the plan of Table 1, the following amino acids were used in the quantities indicated: Boc-DTrp (1.09 g for each of the three couplings), Boc-Val 0.78 g),Boc-(O-2'-bromobenzyloxycarbonyl)-Tyr(1.78 g), cyclohexyl Boc-aspartate (1.12 g) and Boc-tosyl-arginine (1.54 g).

TABLE 1

| Plan for an automatic coupling cycle | | |
|---|---|---|
| 1 | Washing; methylene chloride | 1 × 1' |
| 2 | Protective group removal; 40% trifluoroacetic acid in methylene chloride | 1 × 5' |
| 3 | As above | 1 × 15' |
| 4 | Washing; methylene chloride | 3 × 1' |
| 5 | Neutralization; 5% diisopropylethylamine in methylene chloride | 2 × 1' |
| 6 | Washing; methylene chloride | 3 × 1' |
| 7 | Coupling; anhydride of the amino acid in methylene chloride/dimethylformamide | 1 × 60' |
| 8 | Washing; methylene chloride | 2 × 1' |
| 9 | Washing; isopropanol | 2 × 2' |
| 10 | Washing; methylene chloride | 3 × 1' |

After the last coupling, the protective group removal cycle is repeated, the resin is taken out of the reactor and dried in vacuo over potash, giving 3.60 g of product. This is then followed by the detachment from the resin and simultaneous protective group removal from the side chains with anhydrous hydrofluoric acid. 2 g of the peptide-resin are placed in a Teflon reactor with 2 ml of anisole and 0.2 ml of dimethyl sulfide, the mixture is cooled to −50° C. and 20 ml of anhydrous hydrofluoric acid are distilled in, and magnetic stirring is then maintained in an ice bath for 60 minutes. The hydrofluoric acid is removed by blowing with nitrogen, and the crude product is dried for 2 hours under suction, washed with ethyl ether (2×15 ml) and extracted in 50% acetic acid (3×15 ml) and filtered through a Gooch filter to remove the exhausted resin. The crude product solution thus obtained is concentrated to a small volume in a rotary evaporator and directly loaded on an LH 20 column (2.5×100 cm) and eluted by gravity with 1/1 0.2 M acetic acid/acetonitrile (2 liters), collecting fractions of 10 ml. The peptide-containing fractions are identified by the UV plot (245 nm) of the effluent, combined, concentrated to a small volume in a rotary evaporator and lyophilized, giving 450 mg of crude product. For the final purification of the product by high-pressure liquid chromatography, 100 mg of the crude product are dissolved in 4 ml of an 8:2 aqueous solution of 0.05% trifluoroacetic acid/acetonitrile; the clear solution thus obtained is loaded on an RP 18 column (1.5×15 cm) and eluted with a gradient of acetonitrile containing 0.05% trifluoroacetic acid against 0.05% trifluoroacetic acid from 20 to 80% in 120 minutes at a flow of 10 ml/minute, with UV detection at 254 nm. The product comes out in about 25 minutes; the homogeneous fractions are combined, concentrated and lyophilized, giving 26 mg of product. HPLC characterization: 3.9×150 mm C 18 Waters Delta-Pak column, 20 to 80% gradient of acetonitrile against 0.05% trifluoroacetic acid in 20 minutes, flow 1 ml/minute, UV detection at 210 nm: RT=8.3 minutes, HPLC purity=98.0%.

EXAMPLE 2

Synthesis of the heptapeptide having the following sequence:

H-Asp-Tyr-DTrp-Val-DTrp-DTrp-DTrp-NH₂

1.0 g of "resin for amide peptides by the Fmoc strategy" (CH₃O-Ph(1,4)-CH(NH-Fmoc)-Ph(1,4)-O-(CH₂)₃-CONH-CH(CH₃)-CONH-CH₂-Ph-polymer; Bachem, Switzerland) carrying 0.50 milliequivalent/g of amine groups is placed in the reactor of a Labortec SP 640 semiautomatic synthesizer. The hydrolysis of the fluorenylmethoxycarbonyl (Fmoc) group with 20% piperidine in dimethylformamide (DMF) is carried out automatically according to the plan indicated in Table 2, cycles 1 to 7.

TABLE 2

Plan for an automatic coupling cycle according to the "Fmoc" strategy

| | | |
|---|---|---|
| 1 | Protective group removal; 20% piperidine in DMF | 1 × 3' |
| 2 | As above | 1 × 7' |
| 3 | Washing; methylene chloride (DCM) | 2 × 1' |
| 4 | Washing; DMF | 2 × 1' |
| 5 | Washing; isopropanol | 2 × 1' |
| 6 | Washing; DMF | 2 × 1' |
| 7 | Washing; DCM | 2 × 1' |
| 8 | Pre-equilibration; Fmoc-amino acid in 2:1 DCM/DMF + HOBt | 2' |
| 9 | Coupling; DCC (1M in 2:1 DCM/DMF) | 90' |
| 10 | Washing; isopropanol | 1 × 1' |
| 11 | Washing; DMF | 1 × 1' |
| 12 | Washing; DCM | 1 × 1' |
| 13 | Washings; repeating from 10 twice more | |

This is followed by coupling of the first D-tryptophan by the active ester technique with hydroxybenzotriazole (HOBt) obtained "in situ" by means of dicyclohexylcarbodiimide (DCC). 1.5 milliequivalents (3-fold excess with respect to the amine groups of the resin) of Fmoc-D-tryptophan (0.639 g) and 2 milliequivalents of HOBt (0.310 g) are dissolved in 12 ml of 2:1 DCM/DMF, transferred into the reactor of the apparatus and, after pre-equilibration for 2 minutes with stirring, 1.5 ml of 1 M DCC in 2:1 DCM/DMF (equal to 1.5 milliequivalents) are added, thus initiating the automatic coupling cycle (line 9 in Table 2). At the end of the cycle described in the table, the Kaiser test is carried out on an aliquot of resin; if the degree of incorporation of the amino acid is greater than 99%, the automatic protective group removal from the amine group is carried out; otherwise, the coupling is repeated. For the successive couplings, always according to the plan in Table 2, the following amino acids were used in the quantities indicated: Fmoc-DTrp (0.639 g for each of the 3 further couplings), Fmoc-valine (0.509 g), Fmoc-tyrosine t-butyl ether (0.689 g) and Fmoc-t-butyl aspartate (0.617 g). After the last coupling, the protective group removal cycle is repeated, the resin is taken out of the reactor and dried in vacuo over potash, giving 1.650 g of product. This is then followed by the detachment of the peptide from the resin and simultaneous protective group removal from the side chains by trifluoroacetic acid (TFA). 1.5 g of peptide-resin are placed into a small flask containing 30 ml of a solution consisting of 27:1.5:1.5 (volume/volume) TFA/ethanedithiol/p-cresol and the mixture is maintained for 2 hours in a water bath at 35° C. with magnetic stirring. To precipitate the crude product, 10 volumes of ethyl ether and 5 volumes of petroleum ether, both cooled to 0° C., are added. The mixture is kept overnight at −78° C. and filtered over a porous funnel-shaped filter, giving 350 mg of crude crystalline product. For the purification by high-pressure liquid chromatography, the procedure of Example 1 is followed, giving 12 mg of product; characterization by HPLC analysis (conditions as described in Example 1): Rt=12.6 minutes, HPLC purity=98%.

Further non-limiting examples of compounds according to the general formula I included in the present invention are:

| | |
|---|---|
| H—Asp—Tyr—DTrp—Val—DTrp—DTrp—Tyr—NH₂ | Rt = 11.7' |
| H—Asp—Tyr—DTrp—Val—DTrp—DTrp—Arg—NH₂ | Rt = 9.9' |
| H—Thr—Asp—Tyr—DTrp—Val—DTrp—DTrp—Arg—NH₂ | Rt = 9.6' |
| H—Arg—Asp—Tyr—DTrp—Val—DTrp—DTrp—Met—NH₂ | Rt = 11.0' |
| H—Lys—Asp—Tyr—DTrp—Val—DTrp—DTrp—Arg—NH₂ | Rt = 8.8' |
| H—Arg—Asp—Tyr—DTrp—Val—DTrp—DTrp—Phe—NH₂ | Rt = 11.7' |
| H—Arg—Asp—Ser—DTrp—Val—DTrp—DTrp—Met—NH₂ | Rt = 10.5' |
| H—Asp—Ser—DTrp—Val—DTrp—DTrp—Met—NH₂ | Rt = 11.3' |
| H—Lys—Asp—Met—DTrp—Val—DTrp—DTrp—Arg—NH₂ | Rt = 8.7' |
| H—Arg—Asp—Ser—DTrp—Val—DTrp—DTrp—Arg—NH₂ | Rt = 8.2' |
| H—Asp—Tyr—DTrp—Val—DTrp—DTrp—Met—NH₂ | Rt = 12.3' |
| H—Asp—Tyr—DTrp—Val—DTrp—Trp—Arg—NH₂ | Rt = 9.4' |
| H—Asp—Trp—DTrp—Val—DTrp—DTrp—Arg—NH₂ | Rt = 10.9' |
| H—Asp—DTrp—DTrp—Val—DTrp—DTrp—Arg—NH₂ | Rt = 9.4' | where the HPLC retention time (Rt) was determined as in Example 1.

Biological activity

The capacity of the peptides described in the present invention of interacting with the neurokinin A receptor as agonists or antagonists was evaluated by means of an in vitro assay using a preparation, in which the biological response produced by tachykinin and related peptides is exclusively determined by the neuro-kinin A receptor (NK-2 receptor). Such a preparation is the isolated vas deferens of rats, where the tachykinins produce a potentiation of the contractions caused by the intramural nerves following an electrical stimulation. The determination of the activity of the peptides in this preparation was carried out as described by Rovero et al. (Neuropeptides 10, 355, 1987). The agonistic activity of the peptides assayed is expressed as $pD_2$, which represents the antilogarithm of the molar concentration of agonist which produces 50% of the maximum effect. The antagonistic activity is expressed as $pA_2$, which represents the antilogarithm of the molar concentration of antagonist which produces a dose ratio equal to 2 between two equally effective doses of agonist. The pD$_2$ were calculated according to Van Rossum (Arch. Int. Pharmacodyn. 143, 249, 1963), and the pA$_2$ were calculated from the analysis of the Schild plot (O. Arunlakshana and H. O. Schild, Br. J. Pharmacol., 14, 48, 1959). The following results were obtained:

TABLE 3

| Agonist or antagonist activity of the peptides described on the NK-2 receptor in the isolated vas deferens of rats | | |
|---|---|---|
| Peptide | pD$_2$ | pA$_2$ |
| NKA | 6.64 | n.a. |
| NKA(4-10) | 5.98 | n.a. |
| H—Asp—Tyr—DTrp—Val—DTrp—DTrp—DTrp—NH$_2$ | n.a. | 6.81 |
| H—Asp—Tyr—DTrp—Val—DTrp—DTrp—Tyr—NH$_2$ | n.a. | 6.72 |
| H—Asp—Tyr—DTrp—Val—DTrp—DTrp—Arg—NH$_2$ | n.a. | 6.60 |
| H—Thr—Asp—Tyr—DTrp—Val—DTrp—DTrp—Arg—NH$_2$ | n.a. | 6.60 |
| H—Arg—Asp—Tyr—DTrp—Val—DTrp—DTrp—Met—NH$_2$ | n.a. | 6.60 |
| H—Arg—Asp—Tyr—DTrp—Val—DTrp—DTrp—Arg—NH$_2$ | n.a. | 6.50 |
| H—Lys—Asp—Tyr—DTrp—Val—DTrp—DTrp—Arg—NH$_2$ | n.a. | 6.47 |
| H—Arg—Asp—Tyr—DTrp—Val—DTrp—DTrp—Phe—NH$_2$ | n.a. | 6.24 |

The agonists produce a potentiation of the contractions caused by the nerve of the isolated vas deferens of rats. The antagonistic activity is evaluated as the capacity of the product to produce a parallel displacement towards the right of the concentration/response curve of neurokinin A after a contact time of 15 minutes. NKA denotes neurokinin A and NKA(4-10) is the C-terminal heptapeptide fragment of neurokinin A.

It is intended that the method described is only an exemplification given solely as a practical demonstration of the invention, and this invention can be varied in its forms and arrangements without otherwise departing from the scope of the concept which is the basis of this invention.

We claim:

1. A synthetic peptide corresponding to the following formula:

X-Asp-Y-DTrp-Val-DTrp-Z-K-NH$_2$ where:
X = H, Arg, Lys, Thr
Y = Tyr
Z = DTrp
K = Arg, Phe, DTrp, Tyr, Met
and pharmaceutically acceptable salts thereof.

2. A synthetic peptide having the following formula:

X-Asp-Tyr-DTrp-Val-DTrp-K-NH2 where:
X = H, Arg

K = Arg, Phe, DTrp
and pharmaceutically acceptable salts thereof.

3. An octapeptide as claimed in claim 2 having the following structure:

H-Arg-Asp-Try-DTrp-Val-DTrp-Dtrp-Arg-NH$_2$.

4. A heptapetide as claimed in claim 2 having the following structure:

H-Asp-Tyr-DTrp-Val-DTrp-DTrp-Arg-NH$_2$.

5. An octapeptide as claimed in claim 2 having the following structure:

H-Arg-Asp-Tyr-DTrp-Val-DTrp-DTrp-Phe-NH$_2$.

6. A heptapetide as claimed in claim 2 having the following structure:

H-Asp-Tyr-DTrp-Val-DTrp-DTrp-DTrp-NH$_2$.

7. A heptapetide as claimed in claim 2, having the following structure:

H-Asp-Trp-DTrp-Val-DTrp-DTrp-Arg-NH$_2$.

8. Synthetic peptides as claimed in claim 2 as competitive antogonists against neurokyinin A (NK-2 receptor.

* * * * *